United States Patent
Huh

(10) Patent No.: US 10,741,039 B2
(45) Date of Patent: *Aug. 11, 2020

(54) WELDING PROTECTOR, HEALTHCARE SYSTEM FOR WORKER, AND OPERATING METHOD OF THE SYSTEM

(71) Applicant: OTOS WING.CO., LTD., Geumcheon-gu, Seoul (KR)

(72) Inventor: Moon Young Huh, Seoul (KR)

(73) Assignee: OTOS WING.CO., LTD., Geumcheon-Gu, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/734,848

(22) Filed: Jan. 6, 2020

(65) Prior Publication Data

US 2020/0143652 A1    May 7, 2020

Related U.S. Application Data

(63) Continuation of application No. 16/299,977, filed on Mar. 12, 2019, now Pat. No. 10,559,182.

(30) Foreign Application Priority Data

Mar. 14, 2018    (KR) ........................ 10-2018-0029928

(51) Int. Cl.
   *G08B 21/02* (2006.01)
   *A61F 9/06* (2006.01)

(52) U.S. Cl.
   CPC ................ *G08B 21/02* (2013.01); *A61F 9/06* (2013.01)

(58) Field of Classification Search
   CPC combination set(s) only.
   See application file for complete search history.

(56) References Cited

U.S. PATENT DOCUMENTS

| 4,049,952 | A | * | 9/1977 | Forsslund | ............... | G04F 1/005 |
| | | | | | | 377/16 |
| 10,559,182 | B2 | * | 2/2020 | Huh | ........................ | G08B 21/02 |

(Continued)

FOREIGN PATENT DOCUMENTS

| KR | 2000-0065634 A | 11/2000 |
| KR | 101050708 B1 | 7/2011 |

(Continued)

OTHER PUBLICATIONS

Office Action dated Feb. 12, 2019 in Korean Patent Application No. 10-2018-0029928, filed Mar. 14, 2018, 5 pages. No English translation available.

(Continued)

*Primary Examiner* — Travis R Hunnings
(74) *Attorney, Agent, or Firm* — Kilpatrick Townsend & Stockton LLP

(57) ABSTRACT

Provided are a welding protector, a worker healthcare system, and an operating method of the system.

The welding protector includes a sensor generating a sensing signal obtained by sensing a wearing state of the welding protector worn by a worker; a memory storing at least one instruction; and a processor configured to execute the at least one instruction to generate a feedback signal, wherein the least one instruction includes information for identifying based on the sensing signal whether the worker is to perform a welding operation.

11 Claims, 4 Drawing Sheets

(56) References Cited

U.S. PATENT DOCUMENTS

| | | | | |
|---|---|---|---|---|
| 2005/0001155 A1* | 1/2005 | Fergason | ............... | A61F 9/067 |
| | | | | 250/221 |
| 2008/0158502 A1* | 7/2008 | Becker | ................... | A61F 9/067 |
| | | | | 351/44 |
| 2010/0223706 A1* | 9/2010 | Becker | ................... | A42B 3/30 |
| | | | | 2/8.2 |
| 2011/0246395 A1* | 10/2011 | Dolson | ............. | B01D 53/8631 |
| | | | | 705/400 |
| 2014/0135644 A1 | 5/2014 | Kim | | |
| 2016/0045971 A1* | 2/2016 | Holverson | .......... | B23K 9/1087 |
| | | | | 219/132 |

FOREIGN PATENT DOCUMENTS

| | | |
|---|---|---|
| KR | 2014-0062890 A | 5/2014 |
| KR | 2016-0060435 A | 5/2016 |
| KR | 101676848 B1 | 11/2016 |
| WO | 2009-137379 A1 | 11/2009 |
| WO | 2017-223438 A1 | 12/2017 |

OTHER PUBLICATIONS

Office Action dated Jan. 3, 2020 in German Patent Application No. 102019203131, filed Mar. 7, 2019, 11 pages. No English translation available.

* cited by examiner

WELDING PROTECTOR, HEALTHCARE SYSTEM FOR WORKER, AND OPERATING METHOD OF THE SYSTEM

CROSS-REFERENCE TO RELATED APPLICATION

This application is a continuation of U.S. patent application Ser. No. 16/299,977, filed on Mar. 12, 2019, which claims the benefit of Korean Patent Application No. 10-2018-0029928, filed on Mar. 14, 2018, the disclosures of which are incorporated herein in their entireties by reference.

BACKGROUND

1. Field

One or more embodiments relate to a welding protector, a worker healthcare system, and an operating method of the system.

2. Description of the Related Art

Welding in general is an indispensable tool for metalworking, but fumes, noxious gases, harmful rays, and high temperatures are generated during welding, which can be physically harmful factors to a worker working in a closed environment. Thus, it is necessary to wear a welding protector to protect the welder. The welding protector is used to prevent hazardous factors generated from the working environment and has to be checked beforehand with regard to selection, limitations, and whether it is a tested product that passed examination. The main sources of harmful substances generated in the above-described welding process are welding materials such as base metals, electrodes, and electrode coatings. During welding, base metals and electrodes are heated and metal vapor is released into the air, and the metal vapor is condensed in the air to form fumes. The main factors affecting the rate and amount of generated fumes and the composition of fumes include a welding method, welding conditions, a composition of base metals and welding electrodes, a diameter of welding electrodes, a welding speed, a coating state of a surface of a base metal by painting or plating. Welders must wear a welding protector because health hazards can occur to them in various forms such as metal fume fever, siderosis, pulmonary edema, emphysema, and chronic bronchitis.

The background art described above is a technique that the inventor had to derive embodiments of the present disclosure or technical information acquired during the process of deriving the same, and is not necessarily a technique known to the general public prior to the filing of the embodiments of the present disclosure.

PRIOR ART

Patent Document

KR 2000-0065634

SUMMARY

One or more embodiments include a protector for welders, a healthcare system for workers, and an operating method of the system, in which a duration of a welding operation is calculated, based on a period a welder wears a welding protector, to give feedback on whether to continue or interrupt a welding operation.

Additional aspects will be set forth in part in the description which follows and, in part, will be apparent from the description, or may be learned by practice of the presented embodiments.

According to one or more embodiments, a welding protector includes: a sensor generating a sensing signal obtained by sensing a wearing state of the welding protector worn by a worker; a memory storing at least one instruction; and a processor configured to execute the at least one instruction to generate a feedback signal, wherein the least one instruction includes information for identifying based on the sensing signal whether the worker is to perform a welding operation.

The feedback signal may include at least one of visual information, tactile information, and audible information.

The welding protector may further include a communicator communicating with an external device, wherein the memory is updated by the external device via the communicator.

The external device may include a worker terminal carried by the worker.

According to one or more embodiments, a worker healthcare system includes: a welding protector; and a central control device transmitting or receiving a signal to or from the welding protector via a communication network, wherein the welding protector generates a sensing signal obtained by sensing a wearing state of the welding protector worn by a worker and transmits the sensing signal to the central control device, upon a request by the central control device, wherein the central control device generates a feedback signal about whether to perform a welding operation based on the sensing signal and transmits the feedback signal to the welding protector.

The central control device may transmit the feedback signal including at least one of visual information, tactile information, and audible information to the welding protector.

The central control device may include a worker terminal carried by the worker.

The worker terminal may include a worker healthcare management application and outputs a connection state with respect to the welding protector when the worker healthcare management application is executed.

According to one or more embodiments, an operating method of a worker healthcare system including a welding protector and a central control device transmitting or receiving a signal to or from the welding protector is provided, wherein the operating method includes: receiving a sensing signal obtained by sensing a wearing state of the welding protector worn by a worker; and generating a feedback signal about whether to perform a welding operation based on the sensing signal and transmitting the feedback signal to the welding protector.

The transmitting of the feedback signal may include generating the feedback signal including at least one of visual information, tactile information, and audible information and transmitting the feedback signal to the welding protector.

The central control device may include a worker terminal that includes a worker healthcare application and is carried by the worker, wherein the operating method further includes: executing the worker healthcare application; and outputting a connection state with respect to the welding protector.

In addition, other methods or systems for implementing the present disclosure, and a computer program for executing the methods may be further provided.

In addition to the aforesaid details, other aspects, features, and advantages will be clarified from the following drawings, claims, and detailed description.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
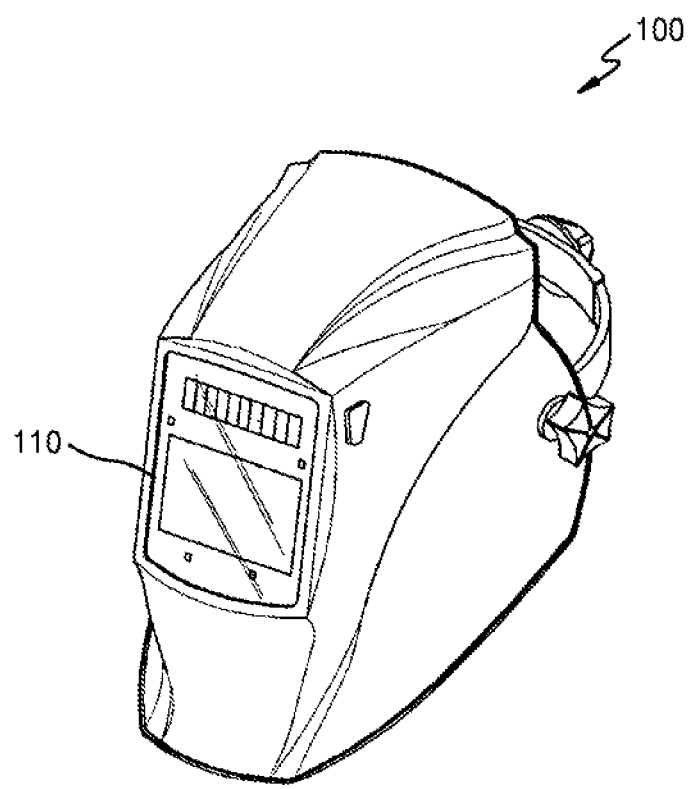
FIG. 1 is a schematic perspective view of a welding protector according to an embodiment of the present disclosure.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items.

The advantages and features of the present disclosure and methods of achieving the advantages and features will be described more fully with reference to the accompanying drawings, in which exemplary embodiments of the present disclosure are shown. However, this is not intended to limit the present disclosure to particular modes of practice, and it is to be appreciated that all changes, equivalents, and substitutes that do not depart from the spirit and technical scope of the present disclosure are encompassed in the present disclosure. In the description of the present disclosure, certain detailed explanations of related art are omitted when it is deemed that they may unnecessarily obscure the essence of the present disclosure.

The terms used in the present specification are merely used to describe particular embodiments, and are not intended to limit the present disclosure. An expression used in the singular encompasses the expression of the plural, unless it has a clearly different meaning in the context. In the present specification, it is to be understood that the terms such as "including" or "having," etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added. While such terms as "first," "second," etc., may be used to describe various components, such components must not be limited to the above terms. The above terms are used only to distinguish one component from another.

The embodiments of the present disclosure will be described below in more detail with reference to the accompanying drawings. Those components that are the same or are in correspondence are rendered the same reference numeral regardless of the figure number, and redundant explanations are omitted.

Figure 2:
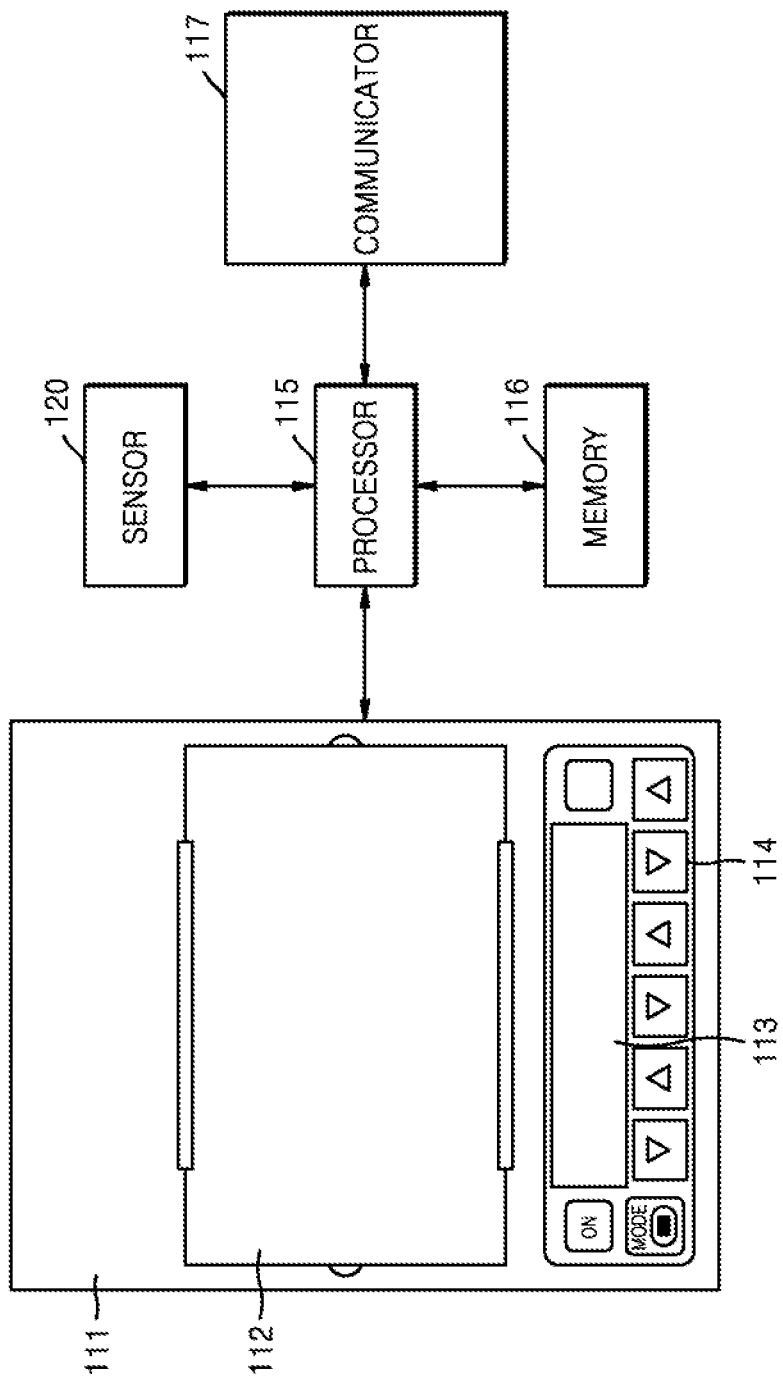
FIG. 2 is a schematic block diagram illustrating a portion of a welding protector according to an embodiment of the present disclosure.

FIG. 1 is a schematic perspective view of a welding protector 100 according to an embodiment of the present disclosure. FIG. 2 is a schematic block diagram illustrating a portion of the welding protector 100 according to an embodiment of the present disclosure. Referring to FIGS. 1 and 2, the welding protector 100 may include a cartridge 110 and a sensor 120. In addition, the cartridge 110 according to the present disclosure may include a main body 111, a liquid crystal screen 112, a display unit 113, a key input unit 114, a memory 115, a processor 116, and a communicator 117.

The welding protector 100 may be in a form covering the face of a worker, and may be formed of a material having a certain strength, for example, a reinforced plastic, but the present disclosure is not limited thereto, and any material that is resistant to elements occurring during welding, such as sparks, may be used.

The cartridge 110 may be mounted on a front surface of the welding protector 100. The main body 111 of the cartridge 110 forms an outer shape of the cartridge 110 and may include the processor 116, the memory 115, and the communicator 117 capable of communicating with an external device (e.g., a worker terminal carried by a worker or a central control device). A density of the liquid crystal screen 112 may be varied according to user's operation or the control of the processor 116. The worker may wear the welding protector 100 to cover the worker's face and then select an appropriate brightness via the liquid crystal screen 112 to perform a welding or cutting operation. The display unit 113 may display a user input state or an operational state of the welding protector 100. The key input unit 114 may receive a user command and transmit the command to the processor 116. The memory 115 may store one or more instructions that may be executed by the processor 116. The memory 115, the processor 116, and the communicator 117 will be described in detail later.

The welding protector 100 may include the sensor 120 generating a sensing signal by sensing a wearing state of a worker. A sensing signal generated using the sensor 120 may be transmitted to the processor 116. According to an embodiment, the sensor 120 may include an optical transmitter (not shown) and a light receiver (not shown) included as a set, or an illuminance sensor (not shown), a pressure sensor (not shown), or a touch sensor (not shown), and the present disclosure is not limited thereto, and various kinds of devices capable of sensing a wearing state of the welding protector 100 by a worker may be used.

In the present embodiment, when a worker is wearing the welding protector 100, the sensor 120 may transmit a sensing signal including a first signal to the processor 116, and when the worker has removed the welding protector 100, the sensor 120 may transmit a sensing signal including a second signal, to the processor 116.

When the sensor 120 includes an optical transmitter and a light receiver, the optical transmitter may be provided on a first inner lateral surface of the welding protector 100 to transmit light toward a second inner lateral surface thereof.

The optical transmitter may be selected from a variety of light-emitting devices (lamps). For example, an infrared LED may be used, but the present disclosure is not limited thereto, and any device capable of emitting light may be used. The light receiver may be provided on the second inner lateral surface of the welding protector 100 and to face the optical transmitter, and receive light transmitted from the optical transmitter. A photodiode, for example, may be used as the light receiver, but the present disclosure is not limited thereto, and any device capable of receiving light may be used. When a worker is wearing the welding protector 100, the light receiver may transmit a sensing signal including a first signal to the processor 116. When the worker has removed the welding protector 100, the light receiver may transmit a sensing signal including a second signal to the processor 116.

When the sensor 120 includes an illuminance sensor, the illuminance sensor provided inside the welding protector 100 may sense an illuminance inside the welding protector 100. This is due to a difference in an illuminance inside the welding protector 100 between when a worker is wearing the welding protector 100 and when the worker has removed the welding protector 100. When a worker is wearing the welding protector 100, the illuminance sensor may transmit a sensing signal including a first signal to the processor 116. When the worker has removed the welding protector 100, the illuminance sensor may transmit a sensing signal including a second signal to the processor 116.

When the sensor 120 includes a pressure sensor, a pressure sensor provided inside the welding protector 100 may sense a pressure inside the welding protector 100. This is due to a difference in a pressure inside the welding protector 100 between when the worker is wearing the welding protector 100 and when the worker has removed the welding protector 100. When the worker is wearing the welding protector 100, the pressure sensor may transmit a sensing signal including a first signal to the processor 116. When the worker has removed the welding protector 100, the pressure sensor may transmit a sensing signal including a second signal to the processor 116.

When the sensor 120 includes a touch sensor, the touch sensor provided inside the welding protector 100 may sense a touch of the welding protector 100. This is due to a difference in a touch state of the welding protector 100 between when the worker is wearing the welding protector 100 and when the welding protector 100 is removed. When the worker is wearing the welding protector 100, the touch sensor may transmit a sensing signal including a first signal to the processor 116. When the worker has removed the welding protector 100, the touch sensor may transmit a sensing signal including a second signal to the processor 116.

The memory 115 may store various types of data and programs for driving and controlling the welding protector 100. A program stored in the memory 115 may include one or more instructions. The program stored in the memory 115 (one or more instructions) may be accessed and executed by the processor 116. Upon receiving an input signal directing to start an operation from the key input unit 114 or receiving a sensing signal including a first signal from the sensor 120, the processor 116 may start accessing the memory 115 and execute a program stored in the memory 115 (one or more instructions). The memory 115 according to an embodiment may include one or more instructions including reference information as information to identify whether to continue or interrupt a welding operation based on a sensing signal.

The memory 115 may include an embedded memory and/or an external memory, and may be a volatile memory such as dynamic random-access memory (DRAM), static random-access memory (SRAM), or synchronous dynamic random access memory (SDRAM); a non-volatile memory such as one-time programmable read-only memory (OTPROM), programmable read-only memory (PROM), erasable PROM (EPROM), electrically erasable programmable read-only memory (EEPROM), mask ROM, flash ROM, a NAND flash memory or a NOR flash memory; a flash drive such as a solid state drive (SSD), a compact flash (CF) card, a Secure Digital (SD) card, a Micro-SD card, a Mini-SD card, an Xd card, or a memory stick; or a storage device such as a hard disk drive (HDD).

The processor 116 may control an overall operating state of the welding protector 100. At least one processor 116 may be included, and may be implemented as an array of a plurality of logic gates or as a combination of a general-purpose microprocessor and a memory 115 in which a program executable in the above microprocessor is stored. In addition, it will be obvious to those skilled in the art that the processor 116 may be implemented in other forms of hardware.

In detail, the processor 116 may receive a sensing signal including a first signal and a second signal to calculate a wearing time based on a wearing state of the welding protector 100 by the worker, and may generate a feedback signal inducing to remove the welding protector 100 based on a wearing time exceeding reference information, for example, a reference time, and may generate a feedback signal inducing to continue operation when the reference time is not exceeded.

The processor 116 may calculate a wearing time of the welding protector 100 by the worker by cumulatively counting a time that a first signal is received, starting from a time when an input signal of the key input unit 114 that is input right before the worker put on the welding protector 100. When a second signal is received during the cumulative counting, the cumulative counting of the first signal may be interrupted, and when a first signal is received again, the cumulative counting of the first signal may be resumed.

A feedback signal may include a signal that is perceivable by a worker who is wearing the welding protector 100, to induce removal of the welding protector 100. The feedback signal may also include a signal perceivable by a worker, to induce the worker wearing the welding protector 100 to continue operation.

The feedback signal may be output via the liquid crystal screen 112 as visual information to be viewed by the worker. A vibration generating element (for example, a motor, etc.) (not shown) may be provided, and a motor that has received a feedback signal may generate a vibration (tactile information) to be sensed by the worker in a tactile manner. In addition, a voice output device (for example, a speaker) (not shown) may be included, and a speaker that has received a feedback signal may generate a voice to be audibly sensed by the worker. An output format of a feedback signal as described above may be stored in the memory 115 as, for example, a textual form indicating that the welding protector 100 is to removed or the operation may be continued, and/or a vibration cycle or an intensity and number of times of a vibration showing that the welding protector 100 is to be removed or the operation may be continued, and/or a voice format indicating that the welding protector 100 is to be removed or the operation may be continued, and the output format of a feedback signal may be executed by the processor 116.

Figure 3:
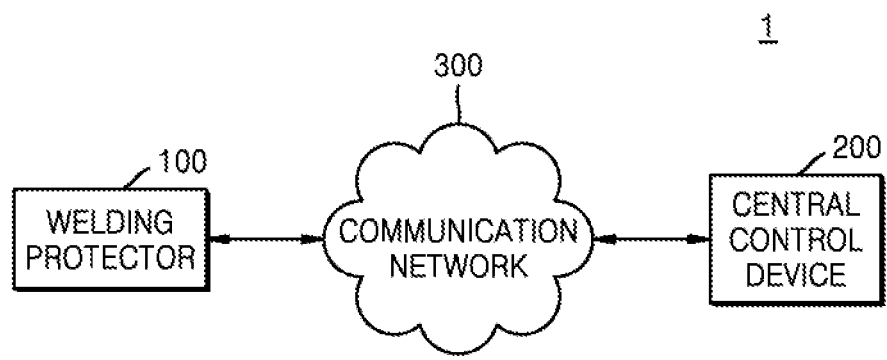
FIG. 3 is a schematic view for describing a worker healthcare system, according to an embodiment of the present disclosure.

The communicator 117 may be linked with a communication network 300 (FIG. 3) and provide a communication interface to provide, in the form of packet data, a transmission/reception signal between the welding protector 100 and an external device (a worker terminal equipped with a worker healthcare application or a central control device 200 of FIG. 3). Furthermore, the communicator 117 may perform a function of receiving a certain information request signal from an external device and transmitting information processed by the welding protector 100 to an external device. A communication network refers to a medium connecting the welding protector 100 to an external device, and may include a path providing a connection path via which the welding protector 100 accesses an external device to transmit or receive information. In addition, the communicator 117 may be a device including hardware and software needed to transmit or receive a signal such as a control signal or a data signal via wired or wireless connection to another network device. In the present embodiment, the communicator 117 may receive a signal for updating the memory 115 from an external device, and update data or programs stored in the memory 115 by using the processor 116.

According to another embodiment, a camera (not shown) may be mounted outside the welding protector 100 to capture an image related to a working environment, and the processor 116 may compare the image of the working environment with a reference image stored in the memory 115, and may generate a feedback signal inducing to leave the working environment when the working environment is dangerous (for example, due to fire, damage or injury). In addition, the feedback signal may be transmitted to an institution capable of eliminating the dangerous environment together with the image of the working environment, such as a fire station or a hospital, so that the institution senses the feedback signal and takes follow-up measures. In the present embodiment, a feedback signal inducing to remove the welding protector 100 or continue operation while having removed the welding protector 100 or while wearing the welding protector 100 may be different in form from a feedback signal inducing to leave the working environment.

FIG. 3 is a schematic view for describing a worker healthcare system 1, according to an embodiment of the present disclosure. Descriptions provided above with reference to FIGS. 1 and 2 will be omitted herein. Referring to FIG. 3, the worker healthcare system 1 may include a welding protector 100, a central control device 200, and a communication network 300.

The welding protector 100 is worn by a worker to protect the worker from a dangerous working environment, and may be in a form covering the face of the worker, and may include a cartridge 110 and a sensor 120.

The sensor 120 sensing a wearing state of the welding protector 100 worn by the worker and generating a sensing signal may be included in the welding protector 100. When the worker is wearing the welding protector 100, the sensor 120 may generate a sensing signal including a first signal, and when the worker has removed the welding protector 100, the sensor 120 may generate a sensing signal including a second signal.

The welding protector 100 may transmit a sensing signal including a first signal and a second signal to the central control device 200 via the communication network 300 upon a request by the central control device 200. The welding protector 100 may also periodically transmit a sensing signal including a first signal and a second signal to the central control device 200 via the communication network 300 also without a request from the central control device 200.

According to another embodiment, a camera (not shown) may be mounted outside the welding protector 100 to capture an image related to a working environment, and the image of the working environment may be transmitted to the central control device 200 via the communication network 300. This may be performed to protect the worker from possible dangers that may occur during an operation (for example, fire, damage or injury).

The central control device 200 may receive a sensing signal including a first signal and a second signal from the welding protector 100 to calculate a wearing time, based on a wearing state of the welding protector 100 worn by the worker, may generate a feedback signal inducing to remove the welding protector 100 based on a wearing time exceeding reference information, for example, a reference time, and may generate a feedback signal inducing the worker to continue operation when the reference time is not exceeded and transmit the feedback signal to the welding protector 100.

The feedback signal generated using the central control device 200 and transmitted to the welding protector 100 via the communication network 300 may be output via the liquid crystal screen 112 of the welding protector 100 as visual information to be viewed by the worker. A vibration generating element (for example, a motor, etc.) (not shown) may be provided, and a motor that has received a feedback signal may generate a vibration (tactile information) to be sensed by the worker in a tactile manner. In addition, a voice output device (for example, a speaker) (not shown) may be included, and a speaker that has received a feedback signal may generate a voice to be audibly sensed by the worker.

According to the present embodiment, the central control device 200 may include a worker terminal carried by a worker. The worker terminal may access the central control device 200 to execute and/or display a worker healthcare application provided by the central control device 200, and the central control device 200 that has received connection identification information (ID) and a password of a worker via the worker terminal may perform worker authentication regarding the worker healthcare application, and when unique information of the welding protector 100 to be worn by a worker is input, a connection state with respect to the welding protector 100 that the worker is wearing may be output on the worker terminal. Then, the worker terminal may output a feedback signal generated by executing a function of the central control device 200, not only on the welding protector 100 but also on the worker terminal.

The communication network 300 performs a function of connecting the welding protector 100 with the central control device 200. That is, the communication network 300 may refer to a communication network that provides a connection path via which the welding protector 100 is connected to the central control device 200 and transmits or receives information. The communication network 300 may be a wired network such as Local Area Networks (LAN), Wide Area Networks (WAN), Metropolitan Area Networks (MAN), Integrated Service Digital Networks (ISDN), wireless LANs, Code Division Multiple Access (CDMA), and Bluetooth, but the present disclosure is not limited thereto.

Figure 4:
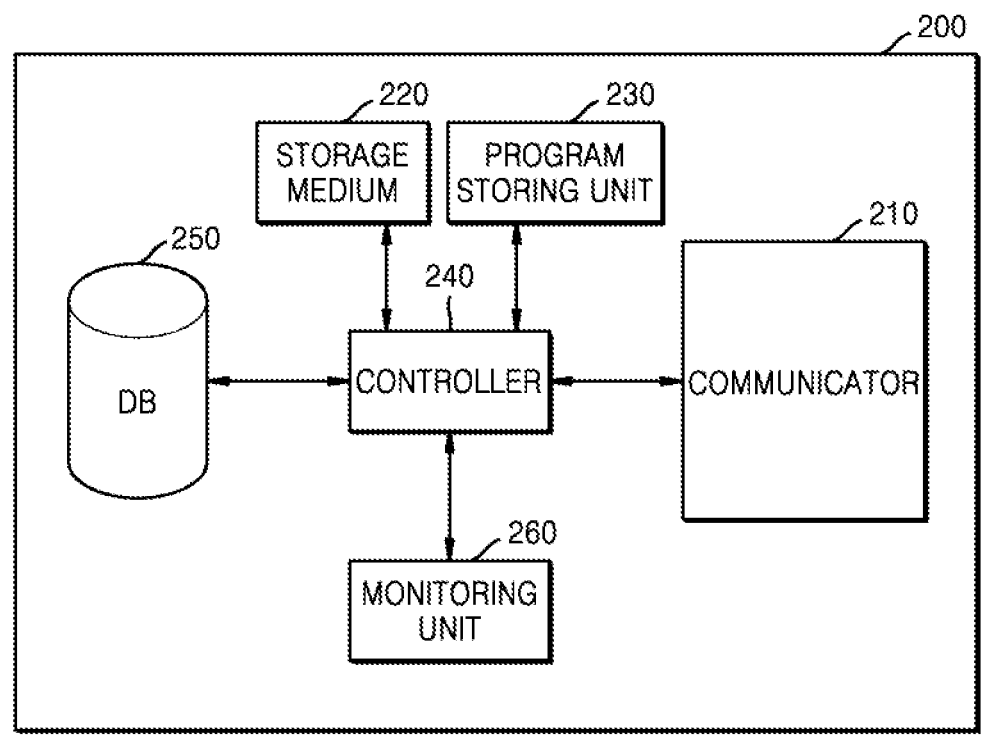
FIG. 4 is a schematic view for describing a structure of a central control device of the worker healthcare system of FIG. 3.

FIG. 4 is a schematic view for describing a structure of a central control device of the worker healthcare system 1 of FIG. 3. Referring to FIG. 4, the central control device 200 may include a communicator 210, a storage medium 220, a program storing unit 230, a controller 240, a database 250, and a monitoring unit 260. The central control device 200 according to the present embodiment may include a worker terminal in which a worker healthcare application is loaded.

The communicator 210 may be linked with the communication network 300 and provide a communication interface to provide a transmission/reception signal between the central control device 200 and the welding protector 100 in the form of packet data. Furthermore, the communicator 210 may perform a function of receiving a certain information signal from the welding protector 100 and transmitting the information signal processed by the monitoring unit 260 (for example, a feedback signal) to the welding protector 100. A communication network refers to a medium connecting the central control device 200 to the welding protector 100, and may include a path providing a connection path via which the welding protector 100 accessed the central control device 200 to transmit or receive information. In addition, the communicator 210 may be a device including hardware and software needed to transmit or receive a signal such as a control signal or a data signal via wired or wireless connection to another network device.

The storage medium 220 performs a function of temporarily or permanently storing data processed by the controller 240. The storage medium 220 may include magnetic storage media or flash storage media, but the present disclosure is not limited thereto. The storage medium 220 may include an internal memory and/or an external memory, and may be a volatile memory such as DRAM, SRAM, or SDRAM; a flash memory such as OTPROM, PROM, EPROM, EEPROM, mask ROM, flash ROM, a NAND flash memory or a NOR flash memory; a flash drive such as an SSD, a CF card, an SD card, a Micro-SD card, a Mini-SD card, an Xd card, or a memory stick; or a storage device such as an HDD.

The program storing unit 230 includes control software to perform an operation of requesting a sensing signal from the welding protector 100 and receiving the same, an operation of calculating a wearing time of the welding protector 100 worn by a worker, from the sensing signal, an operation of generating a feedback signal indicating a result of identifying whether a welding operation is to be performed based on the wearing time, an operation of transmitting a feedback signal to the welding protector 100, an operation of receiving an image of a working environment from the welding protector 100, an operation of identifying whether the image of the working environment indicates a dangerous environment or the like.

The database 250 may include a feedback management database that stores feedback signals provided by the central control device 200. The feedback management database may include a reference operation time indicating a time of an operation performed while the welding protector 100 is worn, wherein the reference operation time is used to induce removal of the welding protector 100 or continuation of operation, a reference image, based on which a dangerous work environment may be identified, a feedback signal that may be output as visual information to be viewed by the worker, a feedback signal that may be output as tactile information to be sensed by the worker (for example, a vibration intensity, a vibration frequency, a number of times of vibration, etc.), and a feedback signal that may be output as audible information to be heard by the worker.

The database 250 may further include a worker database that stores worker information. Herein, the worker database may store worker information about a worker who is to wear the welding protector 100. The worker information may include basic information about the worker such as the worker's name, affiliation, personal information, gender, age, contact information, e-mail address, and address, and authentication information (login information) such as an ID (or e-mail address) and password information, information related to connection such as a country in which a connection of the welding protector 100 is made, a connection location, information on a device used for connection, a network environment via which the connection is made, and the like. In addition, the worker database may include unique information of the welding protector 100 (e.g., a serial number of the welding protector 100 or information indicating the same) assigned to a worker, unique information of each of various welding protectors 100 (when the welding protector 100 is not assigned to a worker, unique information of the welding protector 100 is input by the worker), and the like. In addition, the worker database may include history information of an operation done by the worker wearing the welding protector 100 (date, cumulative wearing time, removal time, etc.), unique information of the welding protector 100 worn by the worker, or the like.

The monitoring unit 260 may receive a sensing signal including a first signal and a second signal from the welding protector 100 to calculate a wearing time, based on a wearing state of the welding protector 100 worn by the worker, and may generate a feedback signal inducing to remove the welding protector 100 based on a wearing time exceeding reference information, for example, a reference time, and may generate a feedback signal inducing the worker to continue operation when the reference time is not exceeded and transmit the feedback signal to the welding protector 100.

The worker of the welding protector 100 that has received the feedback signal inducing removal may remove the welding protector 100 that the worker was wearing and take a break, thereby managing the health condition of the worker and improving a welding efficiency of the worker.

The monitoring unit 260 may calculate a wearing time of the welding protector 100 worn by the worker by cumulatively counting a time that a first signal is received, starting from a time when an input signal of the key input unit 114 that is input right before the worker put on the welding protector 100 or a time the welding protector 100 and a worker terminal are connected as the worker executed a worker healthcare application by using the worker terminal. When a second signal is received during the cumulative counting, the cumulative counting of the first signal may be interrupted, and when a first signal is received again, the cumulative counting of the first signal may be resumed, thereby calculating a wearing time of the welding protector 100.

In addition, the monitoring unit 260 may compare an image of the working environment, received from the welding protector 100, with a reference image and may generate a feedback signal inducing to leave the working environment when the working environment is dangerous (for example, due to fire, damage or injury). In addition, the monitoring unit 260 may send the feedback signal and the image of the working environment to an institution capable of eliminating the dangerous environment, such as a fire station or a hospital, so that the institution senses the feedback signal and takes follow-up measures. A feedback signal inducing to remove the welding protector 100 or continue operation while having removed the welding protector 100 or while wearing the welding protector 100 may be different in form from a feedback signal inducing to leave the working environment.

Figure 5:
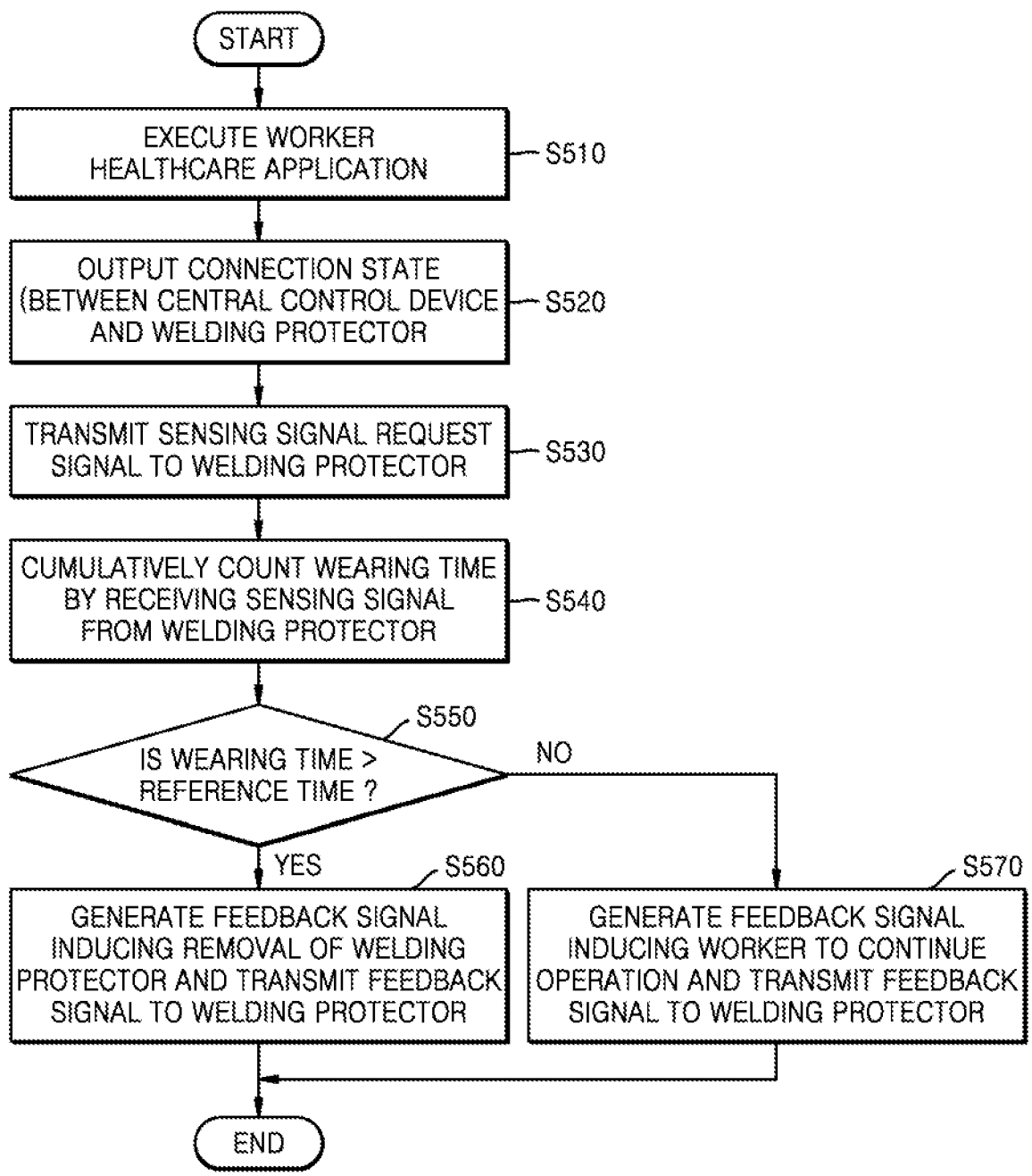
FIG. 5 is a flowchart of an operating method of a worker healthcare system, according to an embodiment of the present disclosure.

FIG. 5 is a flowchart of an operating method of a worker healthcare system according to an embodiment of the present disclosure. Descriptions provided above with reference to FIGS. 1 through 4 will be omitted herein.

Referring to FIG. 5, in operation S510, a worker healthcare application having a function of the central control device 200 and loaded in a worker terminal is executed.

In operation S520, when the worker healthcare application is executed, the central control device 200 outputs information indicating that the central control device 200 is connected to the welding protector 100 to be worn by a worker. When the central control device 200 is not connected to the welding protector 100 to be worn by the worker, the worker may input unique information of the welding protector 100 that the worker is to wear, and the central control device 200 receiving the unique information may output information indicating that the central control device 200 is connected to the welding protector 100 to be worn by the worker.

In operation S530, when the central control device 200 and the welding protector 100 are connected, a time counting regarding the welding protector 100 is executed starting from a time of the start of the connection, and the central control device 200 generates a sensing signal request signal and transmits the same to the welding protector 100.

In operation S540, the central control device 200 may receive a sensing signal including first and second signals from the welding protector 100 to cumulatively count a wearing time of the welding protector 100. The first signal may be received when the worker is wearing the welding protector 100, and the second signal may be received when the worker has removed the welding protector 100. From a time when the connection is started, the central control device 200 may cumulatively count a time when the first signal is received to calculate a wearing time of the welding protector 100 worn by the worker. When a second signal is received during the cumulative counting, the cumulative counting of the first signal may be interrupted, and the cumulative counting of the first signal may be resumed when the first signal is received again, thereby calculating a wearing time of the welding protector 100.

In operation S550, the central control device 200 identifies whether the wearing time of the welding protector 100 exceeds a reference time.

In operation S560, when the wearing time of the welding protector 100 exceeds the reference time, the central control device 200 generates a feedback signal inducing removal of the welding protector 100 and transmits the feedback signal to the welding protector 100.

In operation 5570, when the wearing time of the welding protector 100 does not exceed the reference time, the central control device 200 generates a feedback signal inducing the worker to continue operation and transmits the feedback signal to the welding protector 100.

The worker of the welding protector 100 that has received the feedback signal inducing removal may remove the welding protector 100 that the worker was wearing and take a break, thereby managing the health condition of the worker and improving a welding efficiency of the worker.

The operating method of the worker healthcare system may be independently executed within the welding protector 100 by executing a program stored in the memory 115 by using the processor 116. When the operating method is independently executed inside the welding protector 100, a time when a first signal is received is cumulatively counted starting from a time when the worker started wearing the welding protector 100 (the start is made by receiving a key input of the key input unit 114), to thereby calculate a wearing time of the welding protector 100. When the wearing time of the welding protector 100 exceeds a reference time, a feedback signal inducing removal of the welding protector 100 is generated, and when the wearing time of the welding protector 100 does not exceed the reference time, a feedback signal inducing the worker to continue operation may be generated.

The above-described embodiments of the present disclosure can be implemented in the form of a computer program that can be executed by various components on a computer, and such a computer program can be recorded on a computer-readable recording medium. At this time, the computer-readable recording medium may be a magnetic medium such as a hard disk, a floppy disk and magnetic tape, an optical recording medium such as CD-ROM and DVD, a magneto-optical medium such as a floptical disk, or ROM, RAM, a flash memory, and the like, which are specifically configured to store and execute program instructions.

The computer program may be specifically designed and configured for the embodiments of the present disclosure or may be well-known and available to one of ordinary skill in the art. Examples of the computer program are advanced language codes that can be executed by a computer by using an interpreter or the like as well as machine language code made by a compiler.

Uses of the term "the" and other terms similar thereto in the specification of the present disclosure (in particular, in the claims) may correspond to both the singular and plural forms. If a range is described in the present disclosure, individual values belonging to the range are included in the present disclosure (if no contrary description appears in the specification), and each individual value is incorporated into the specification as if it were individually recited herein.

If an order of operations of a method according to the present disclosure is clearly described or there is no contrary description to the order, the operations may be performed in the described order or other appropriate order. The present disclosure is not necessarily limited to the operational order described therein. In addition, all examples or exemplary terms (for example, "etc.") in the present disclosure are simply for describing the present disclosure. Therefore, the scope of the present disclosure is not limited by the examples or exemplary terms therein. Also, it will be understood by those of ordinary skill in the art that numerous changes and adaptations in form and details may be made therein without departing from the spirit and scope of the present disclosure as defined by the following claims.

Therefore, the scope of the present disclosure is defined not by the detailed description of the present disclosure but by the appended claims, and all differences within the scope will be construed as being included in the present disclosure.

According to the embodiments, a time of a welding operation may be calculated based on a wearing time of a welding protector worn by a worker to give feedback on whether to continue or interrupt the welding operation. Accordingly, when the welding operation is to be interrupted, the worker may interrupt the welding operation and take a break, thus managing the health condition of the worker.

In addition, by giving feedback on whether to continue or interrupt a welding operation by calculating a wearing time of the welding protector worn by the worker, in a case when the worker is to interrupt the welding operation, the worker may interrupt the welding operation and take a break, thus increasing a welding efficiency of the worker.

The effects according to the present disclosure are not limited to the above-described ones, and other effects not mentioned herein will be apparent to one of ordinary skill in the art from the description of the disclosure.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the disclosure as defined by the following claims.

What is claimed is:

1. A welding protector comprising:
a sensor generating a sensing signal obtained by sensing a wearing state;
a memory storing at least one instruction; and
a processor configured to execute the at least one instruction to generate a feedback signal,
wherein the least one instruction comprises information for identifying based on the sensing signal.

2. The welding protector of claim 1, wherein the feedback signal comprises at least one of visual information, tactile information, and audible information.

3. The welding protector of claim 1, further comprising a communicator communicating with an external device,
wherein the memory is updated by the external device via the communicator.

4. The welding protector of claim 3, wherein the external device comprises a worker terminal carried by the worker.

5. A worker healthcare system comprising:
a welding protector; and
a central control device transmitting or receiving a signal to or from the welding protector via a communication network,
wherein the welding protector generates a sensing signal obtained by sensing a wearing state and transmits the sensing signal to the central control device, upon a request by the central control device,
wherein the central control device generates a feedback signal based on the sensing signal and transmits the feedback signal to the welding protector.

6. The worker healthcare system of claim 5, wherein the central control device transmits the feedback signal comprising at least one of visual information, tactile information, and audible information to the welding protector.

7. The worker healthcare system of claim 5, wherein the central control device comprises a worker terminal carried by the worker.

8. The worker healthcare system of claim 7, wherein the worker terminal includes a worker healthcare management application and outputs a connection state with respect to the welding protector when the worker healthcare management application is executed.

9. An operating method of a worker healthcare system including a welding protector and a central control device transmitting or receiving a signal to or from the welding protector, the operating method comprising:
receiving a sensing signal obtained by sensing a wearing state; and
generating a feedback signal based on the sensing signal and transmitting the feedback signal to the welding protector.

10. The operating method of claim 9, wherein the transmitting of the feedback signal comprises generating the feedback signal including at least one of visual information, tactile information, and audible information and transmitting the feedback signal to the welding protector.

11. The operating method of claim 9, wherein the central control device comprises a worker terminal that includes a worker healthcare application and is carried by the worker,
wherein the operating method further comprises:
executing the worker healthcare application; and
outputting a connection state with respect to the welding protector.

* * * * *